United States Patent [19]

Johnsen et al.

[11] 4,128,543

[45] Dec. 5, 1978

[54] PROCESS FOR PREPARING ALCOHOL SOLUBLE CONDENSATES OF ABIETIC ACID AND A PROTEIN HYDROLYSATE

[75] Inventors: Vernon L. Johnsen, La Grange; Elaine S. Stern, Evanston, both of Ill.

[73] Assignee: Inolex Corporation, Chicago, Ill.

[21] Appl. No.: 761,668

[22] Filed: Jan. 24, 1977

[51] Int. Cl.$^2$ .............................. A23J 1/10; C07G 7/00
[52] U.S. Cl. .............................. 260/123.7; 260/112 B; 260/112 R; 260/121; 424/47; 424/70; 424/71
[58] Field of Search ............ 260/112 R, 112 B, 123.7, 260/121; 424/71, 70, 47

[56] References Cited

U.S. PATENT DOCUMENTS

| 2,100,090 | 11/1937 | Sommer et al. | 260/121 |
| 2,151,241 | 3/1939 | Sommer et al. | 260/121 |
| 2,440,555 | 4/1948 | Omohundro et al. | 424/70 |
| 3,954,725 | 5/1976 | Johnsen et al. | 260/112 R |

OTHER PUBLICATIONS

Lamepon PA-TR, Chemische Fabrik.

*Primary Examiner*—Howard E. Schain
*Attorney, Agent, or Firm*—Dressler, Goldsmith, Clement, Gordon & Shore, Ltd.

[57] ABSTRACT

Resin-forming condensates of abietic acid and a protein hydrolysate are prepared which are completely soluble in absolute alcohol at a concentration of about 2 percent. An aqueous solution of a water soluble salt of a condensate of abietic acid with a protein hydrolysate is acidified from a pH above about 6 to a pH in the range of about 4 to 5 to precipitate a portion of the condensate while leaving another portion thereof in solution. The precipitated portion of the condensate is the alcohol soluble product of the process.

13 Claims, No Drawings

PROCESS FOR PREPARING ALCOHOL SOLUBLE CONDENSATES OF ABIETIC ACID AND A PROTEIN HYDROLYSATE

BACKGROUND OF THE INVENTION

The present invention relates to novel methods for preparing a resinous material suitable for use in hair sprays, and to the novel hair-holding resinous material created thereby. In addition, it relates to hair-holding compositions such as hair sprays, and the like.

Resinous materials for use in hair sprays must satisfy several requirements. In terms of functionality, materials are sought which deposit from solution, and preferably from alcohol solution, to form a non-tacky, non-greasy film which is unaffected by high humidity and which helps retain a curl when sprayed onto hair. In terms of appearance, it is also desirable that the solution be clear and that the film deposited therefrom be clear so that it does not appreciably alter the appearance and color of the hair. Finally, the deposited film should be easily removable from hair with a shampoo.

U.S. Pat. No. 2,440,555 to Omohundro et al. discloses alcoholic, resin-containing hair treatment solutions in which the resin is an abietic ester, such as ethyl abietate and ethylene glycol ester of abietic acid, or a hydrogenated abietic ester such as hydrogenated methyl abietate. It further discloses that these solutions form a thin protective non-tacky adhesive film of non-greasy characteristics on the hair which can be readily washed off with soap and water. However, it has been found that the films formed by these abietic esters are liquid films which do not have curl holding properties.

It has been proposed to use as the resin in an aqueous hair spray, an abietic acid condensate of a protein hydrolysate; and specifically the condensate sold commercially under the trademark "Lamepon PA-TR" which is a 30% aqueous solution of triethanolamine salt of a condensation product with abietic acid of a protein hydrolysate having an average molecular weight of about 400. The chemical and physical data included in the commercial literature of Lamepon PA-TR indicates that it has many properties which make it suitable for use in a hair dressing. The literature specifically states that for preparations such as hair lotions or hair sprays, which remain on the skin and hair for relatively long periods, as little as 0.1 to 0.2 percent of Lamepon PA-TR may be used in the formulation with good results. However, when it has been attempted to use the free carboxylic acid form of the condensate of Lamepon PA-TR as the major film-forming ingredient in an alcoholic hair-holding solution at the commercially and functionally desirable concentration of about 2 percent of condensate in absolute alcohol, it has been found that some of the condensate precipitates out of solution. This is surprising because no precipitate forms when the free carboxylic acid form of the condensate of Lamepon PA-TR is dissolved in absolute alcohol at a concentration of 20 percent.

In a hair dressing preparation intended for spray application, and particularly for aerosol spray application, the presence of any precipitate tends to clog the dispensing valve and impair the spray application. In addition, a precipitate in the spray solution tends to produce a cloudy deposit on the hair and thereby dulls the hair on application thereto.

SUMMARY OF THE INVENTION

The present invention relates to a method for separating from an abietic acid condensate of a protein hydrolysate a portion having complete solubility in absolute alcohol at a concentration of about 2 percent. The method comprises acidifying an aqueous solution of about 5 to about 25 percent by weight of a water soluble salt of the condensate with abietic acid of a protein hydrolysate having an average molecular weight in the range of about 300 to about 600 from a pH above about 6 to a pH in the range of about 4 to 5 to precipitate a portion of the condensate while leaving another portion thereof in solution. The precipitated portion of the condensate is separated from the acidified solution as the product of the process.

In another embodiment of the invention, the process additionally comprises forming a solution of the precipitated condensate in absolute alcohol having a concentration in the range of about 0.5 to about 5 percent by weight of the precipitated portion of the condensate.

The invention also concerns the use of the products of the novel processes of this invention in hair dressings and hair sprays. Suitable hair dressings are obtained by using the alcoholic solution obtained by the aforementioned process. The invention further includes forming a hair spray by adding a propellant, such as a chlorofluorocarbon, to the alcoholic solution obtained from the proccess.

DETAILED DESCRIPTION

The process of this invention is carried out by acidifying an aqueous solution of about 5 to about 25 percent by weight of a water soluble salt of a condensate with abietic acid of a protein hydrolysate having an average molecular weight in the range of about 4 to 5, to precipitate a portion of the condensate while leaving another portion thereof in solution. The precipitated portion of the condensate may then be separated from the acidified aqueous solution as a product of the process by conventional separation means such as filtration, centrifugation, or decantation. The precipitated portion of the condensate has complete solubility in absolute alcohol at a concentration of about 2 percent as well as at higher concentrations.

A triethanolamine salt of an abietic acid condensate of a protein hydrolysate which is useful in this invention is commercially sold as Lamepon PA-TR by CHEMISCHE FABRIK GRUNAU GMBH, 7918 Jllertissen/Bayern. The protein hydrolysate of this substance is a collagen-based protein hydrolysate. Thus, it has an amino acid content of which at least 50 percent of the amino acid moieties are selected from the group consisting of glycine, proline, and hydroxyproline. The protein hydrolysate has an average molecular weight of about 400 and the condensate has the following formula:

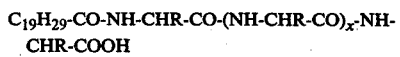

$C_{19}H_{29}\text{-CO-NH-CHR-CO-(NH-CHR-CO)}_x\text{-NH-CHR-COOH}$ wherein $x$ is an integer from 1 to 4, and each R is independently selected from the group consisting of hydrogen and the moieties of the alpha substituents of the natural amino acids of molecular weight higher than that of glycine. Other collagen-based protein hydrolysates may also be used in the condensates of the present invention, such as those having an average molecular weight in the range of about 300 to about 600, or preferably in the range of about 350 to about 500.

In the preferred practice of the invention, the water soluble salt of the condensate is an ammonium salt. Other useful salts also include amine salts and alkali metal salts.

In carrying out the process of the invention, the aqueous solution of the salt of the condensate is acidified to a pH in the range of about 4 to about 5, preferably in the range of about 4.3 to about 4.7, and even more preferably to a pH of about 4.5 to precipitate a portion of the condensate which is completely soluble in absolute alcohol at a concentration in the range of about 0.5 to about 5 percent.

Once the precipitated portion of the condensate has been separated from the acidified aqueous solution, it may be washed and dried, and then dissolved in absolute alcohol to the desired pH to form a hair treatment solution having a concentration in the range of about 0.5 to about 5 percent by weight of the precipitated portion of the condensate. This solution may be formed in one of two ways. It may be formed by direct dissolution to the desired concentration of condensate in the alcohol. Alternatively, it may be formed by dissolving into absolute alcohol a sufficient amount of the separated-precipitated portion of the condensate to form a solution having a concentration in the range of about 20 to about 35 percent by weight of the condensate. Thereafter, this concentrated solution may be further diluted with absolute alcohol to form a second solution having a concentration of the condensate in the range of about 0.5 to about 5 percent by weight of the condensate.

It has been found that a 2 percent alcoholic solution of the portion of an ammonium salt analog of Lamepon PA-TR, which was precipitated from an aqueous solution at a pH of 4.5, has a natural pH of about 3.2. This pH was determined by taking a sample portion of the solution of condensate in absolute alcohol, diluting it with an equal volume of distilled water to form an aqueous solution, and thereafter measuring the pH. If it is so desired, the pH of the solution of the condensate in alcohol may be adjusted by adding a non-aqueous acid or base.

An alternate method for separating the completely alcoholic-soluble fraction of the condensate from solution is to acidify a 15 percent solution of an ammonium salt of the abietic acid condensate of the protein hydrolysate to a pH in the range of about 2.5 to about 3.5 and preferably at about 3.0 to form a precipitate. This precipitate is then separated by conventional means such as filtration, centrifugation, or decantation, and is then washed and dried. The precipitate is then dissolved in absolute alcohol to form a solution of about 15 to about 25 percent, and preferably 20 percent. The pH of the alcoholic solution is then adjusted to a value in the range of about 5 to 6, and preferably to about 5.5 with a base, such as NaOH, to form a second precipitate. The second precipitate may be separated by any of the above-mentioned conventional means, but preferably is separated by centrifugation at a temperature in the range of about −5° C. to about 10° C. and preferably about 2° to about 6° C. The clear solution is decanted off and is adjusted to a pH of about 4.0 with hydrochloric acid. This solution may be diluted to any desired value with the further addition of absolute alcohol, and no precipitate will form.

The alcoholic solution obtained by the above-described method may be incorporated into a hair spray by combining it with an aerosol propellant. The aerosol propellant used in the hair spray is a liquified gas which exerts a total pressure of from about 25 to about 50 pounds per square inch at room temperature. It may be one of a number of halogenated hydrocarbons or mixtures thereof chosen to give a desired vapor pressure. The most satisfactory of these compounds are the halogenated hydrocarbons containing 1 to 5 carbon atoms and more particularly fluorine and chlorine substituted methane and ethane including trichlorofluoromethane, dichlorodifluoro methane, 1,2-dichloro-1,1,2,2-tetrafluoroethane, or the like, or mixtures thereof. Particularly suitable is a 50—50 mixture of trichlorofluoromethane and dichlorodifluoromethane. The amount of propellant depends on the amount of the other ingredients in the composition and should be sufficient to make 100 parts of the composition. In general, the amount of propellant may range from about 49 to 74 weight percent of the total composition.

The propellant may be suitably combined with the alcoholic solution of the condensate by placing the solution in a suitable pressure container fitted with a spray nozzle and pressurizing the solution with the propellant. Other methods of pressurizing the solution may also be used, and are well known to those skilled in the art.

Various conventional additives such as lanolin, non-drying oils, dyes, waxes, pigments, and the like, may be added in small amounts to vary the properties of the hair spray. In addition, a small amount of an alcohol soluble perfume may be added for esthetic appeal.

The compositions of this invention may be sprayed on dry or damp hair to provide a thin transparent film enhancing the natural luster of the hair without imparting a lacquered appearance thereto. The deposited film has sufficient strengh to keep the hair in place, even under conditions of high humidity, but without stiffening the hair. The hair spray dries quickly to a non-tacky state which does not flake on combing but is easily removed by washing with water and a mild soap or commercial shampoo preparations.

EXAMPLES

The following examples serve to illustrate the invention but not limit it.

EXAMPLE 1

An ammonium salt of an abietic acid condensate of a collagen-derived protein hydrolysate having a molecular weight of about 400 was diluted with distilled water to a concentration of about 15 percent. The pH of the diluted solution was in the range of 6 to 7. The pH was adjusted with HCl to a value of 4.5. A heavy, sticky precipitate formed. The supernatant was decanted off and discarded. The precipitate was washed several times with water and a collected condensate in absolute alcohol fraction was dried in a vacuum oven. A 2 percent solution of the condensate was prepared which was initially clear and free from any precipitate. After standing for a few days, the solution remained clear and free from any precipitate.

EXAMPLE 2

The process of Example 1 was repeated with the exception that the pH of the dilute solution of the ammonium salt of the condensate was adjusted to a value of 3.5 with HCl. A heavy, sticky precipitate formed. The supernatant was decanted off and discarded. The precipitate was washed several times with water, and the collected condensate fraction dried in a vacuum oven. A 2 percent solution of the condensate was prepared, which was initially clear and free from a precipitate. After a few days, no precipitation occurred.

EXAMPLE 3

The process of Example 1 was repeated with the exception that the solution of ammonium salt of the condensate was adjusted to a pH of 3.0 with HCl. A precipitate formed and was separated, washed, and dried as was done in Examples 1 and 2. A 2 percent solution of the condensate in absolute alcohol fraction in absolute alcohol was prepared which was initially clear. However, after a few days, a small amount of precipitation occurred in the solution.

EXAMPLE 4

Virgin hair tresses were set on ¾ inch (1.84 cm.) rollers after the hair had been shampooed with an anionic shampoo. After the curls were allowed to dry at ambient conditions overnight, the rollers were removed and the curls sprayed from a pump spray with a 2 percent solution of the abietic condensates of Examples 1, 2, and 3. Each curl was sprayed 25 times from 6 inches (14.7 cm.) away while the curl was rotated. After the curls dried, they were placed in an 80–90% relative humidity cabinet and the curl fall observed.

The best holding was obtained from the material precipitated at a pH of 4.5. The curls sprayed with this condensate dropped only about half the length of the pH 3.0 and the pH 3.5 condensate sprayed curls.

EXAMPLE 5

The set holding of the "pH 4.5" condensate was compared to 2 percent alcoholic solutions of abietic acid and GANTREZ ES-425 which were adjusted to predetermined pH by the addition of a base to the alcoholic solution. The materials tested and the pH to which they were adjusted are set out in the table below.

| 2 percent solution in absolute alcohol of: | |
|---|---|
| 1. "pH 4.5" abietic acid condensate | pH 3.2 |
| 2. Abietic acid | pH 3.0 |
| 3. Abietic acid | pH 4.0 |
| 4. Abietic acid | pH 7.0 |
| 5. Abietic acid | pH 8.0 |
| 6. Gantrez ES-425* | pH 3.4 |
| 7. Gantrez ES-425* | pH 4.2 |
| 8. Gantrez ES-425* | pH 5.7 |
| 9. Gantrez ES-425* | pH 6.9 |

* a butyl monoester of a polymethyl vinyl ester/maleic acid copolymer

The abietic acid condensate was far better than abietic acid at any pH. The Gantrez ES-425 at any pH was slightly better than the condensate. However, the abietic acid condensate is substantive to hair while Gantrex ES-425 is not.

In addition to the set-holding properties, it was noted that the abietic acid sprayed tresses were quite tacky, while the condensate sprayed tresses and the Gantrez sprayed tresses were not.

EXAMPLE 6

A 3 percent solution in absolute alcohol of each of the hair dressings prepared in Example 5 was placed in a preweighed aluminum dish and allowed to dry at ambient conditions. The dishes were then reweighed.

A 5 milliliter solution of 10 percent DUPONOL WAT (triethanolamine lauryl sulfate) at a pH of 7.8 was placed into each dish. After two minutes, the solution was discarded and the dish rinsed with 50 milliliters of water. The procedure was then repeated. The dishes were dried at 105° Centigrade and reweighed. The following table demonstrates the removability of each hair dressing.

| Film on dish from a 3 percent solution in absolute alcohol of: | | Percent of film removed by washing |
|---|---|---|
| 1. "pH 4.5" abietic condensate | pH 3.2 | 55.6 |
| 2. Abietic acid | pH 3.0 | 26.9 |
| 3. " | pH 4.0 | 28.3 |
| 4. " | pH 7.0 | 98.5 |
| 5. " | pH 8.0 | 95.8 |
| 6. Gantrez ES-425 | pH 3.4 | 52.5 |
| 7. " | pH 4.2 | 48.1 |
| 8. " | pH 5.7 | 57.5 |
| 9. " | pH 6.9 | 92.0 |

EXAMPLE 7

3 percent solutions of each of the resins prepared in Example 5 were placed in preweighed aluminum dishes and were allowed to dry at ambient conditions. The dishes were then reweighed. The film-covered dishes were then exposed to 80 to 90 percent relative humidity for 4 hours and were then reweighed. The following table demonstrates the relative hygroscopicity of each of the hair dressings which is shown as a percentage of the moisture uptake by the hair dressing.

| Film on dish from a 3 percent solution in absolute alcohol of: | | Percent of Mositure Uptake |
|---|---|---|
| 1. "pH 4.5" abietci condensate | pH 3.2 | 7.7 |
| 2. Abietic acid | pH 3.0 | 1.2 |
| 3. " | pH 4.0 | 1.5 |
| 4. " | pH 7.0 | 12.1 |
| 5. " | pH 8.0 | 18.8 |
| 6. Gantrez ES-425 | pH 3.4 | 4.2 |
| 7. " | pH 4.2 | 3.7 |
| 8. " | pH 5.7 | 4.8 |
| 9. " | pH 6.9 | 9.0 |

What is claimed is:

1. A process for separating from an abietic acid condensate of a protein hydrolysate a portion having complete solubility in absolute alcohol at a concentration of about 2 percent comprising:
   acidifying an aqueous solution of about 5 to about 25 percent by weight of a water soluble salt of a condensate with abietic acid of a protein hydrolysate having an average molecular weight in the range of about 300 to about 600 from a pH above about 6 to a pH in the range of about 3.5 to about 5 to precipitate a portion of the condensate while leaving another portion thereof in solution; and
   separating and drying the precipitated portion of the condensate from the acidified aqueous solution as a product of the process.

2. The process of claim 1 wherein the condensate has an average formula:

$$C_{19}H_{29}\text{-CO-NH-CHR-CO-(NH-CHR-CO)}_x\text{-NH-CHR-COOH}$$

wherein $x$ is an integer from 1 to 4, and each R is independently selected from the group consisting of hydrogen and the moieties of the alpha substituents of the natural amino acids of molecular weight higher than that of glycine.

3. The process of claim 1 wherein the protein hydrolysate is a collagen-based protein hydrolysate having an amino acid content of which at least 50 percent is selected from the group consisting of glycine, proline, and hydroxyproline.

4. The process of claim 1 wherein the protein hydrolysate has an average molecular weight in the range of about 350 to about 500.

5. The process of claim 1 wherein the protein hydrolysate has an average molecular weight of about 400.

6. The process of claim 1 wherein the water soluble salt of the condensate is an ammonium salt.

7. The process of claim 1 wherein the solution is acidified to a pH of about 4.5.

8. The process of claim 1 wherein the precipitate is separated from the acidified aqueous solution by filtration.

9. The process of claim 1 wherein the precipitate is separated from the acidified aqueous solution by centrifugation.

10. The process of claim 1 wherein the precipitate is separated from the acidified aqueous solution by decantation.

11. A process for separating from an abietic acid condensate of a protein hydrolysate a portion having complete solubility in alcohol at a concentration of about 2 percent comprising:

acidifying an aqueous solution of about 5 to about 25 percent by weight of a water soluble ammonium salt of a condensate with abietic acid of a collagen-based protein hydrolysate having an amino acid content of which at least 50 percent is selected from the group consisting of glycine, proline, and hydroxyproline, the hydrolysate having an average molecular weight in the range of about 350 to 500, from a pH above about 6 to a pH in the range of about 4.5 to precipitate a portion of the condensate while leaving another portion thereof in solution; and separating the precipitated portion of the condensate from the acidified aqueous solution as a product of the process.

12. The product of the process of claim 1.
13. The product of the process of claim 11.

* * * * *